(12) United States Patent
Björling

(10) Patent No.: US 7,662,086 B2
(45) Date of Patent: Feb. 16, 2010

(54) DETECTION AND/OR MONITORING OF DIASTOLIC HEART FAILURE

(75) Inventor: Anders Björling, Solna (SE)

(73) Assignee: St. Jude Medical AB, Jarfalla (SE)

( * ) Notice: Subject to any disclaimer, the term of this patent is extended or adjusted under 35 U.S.C. 154(b) by 361 days.

(21) Appl. No.: 11/628,838

(22) PCT Filed: Jun. 17, 2004

(86) PCT No.: PCT/SE2004/000980

§ 371 (c)(1),
(2), (4) Date: Dec. 6, 2006

(87) PCT Pub. No.: WO2005/123180

PCT Pub. Date: Dec. 29, 2005

(65) Prior Publication Data

US 2008/0262365 A1    Oct. 23, 2008

(51) Int. Cl.
*A61N 1/00*    (2006.01)
(52) U.S. Cl. ........................................ 600/17
(58) Field of Classification Search ........... 607/19, 607/17, 9, 18, 25; 600/322, 335, 323
See application file for complete search history.

(56) References Cited

U.S. PATENT DOCUMENTS

| | | | | |
|---|---|---|---|---|
| 6,221,618 B1 * | 4/2001 | Chien et al. | ................. | 435/7.21 |
| 6,819,950 B2 * | 11/2004 | Mills | ........................... | 600/322 |
| 7,215,996 B2 * | 5/2007 | Noren et al. | ................... | 607/17 |
| 2002/0072683 A1 | 6/2002 | Schroeppel et al. | | |
| 2006/0095085 A1 * | 5/2006 | Marcus et al. | ................. | 607/17 |
| 2008/0234776 A1 * | 9/2008 | KenKnight et al. | ............ | 607/19 |
| 2009/0030292 A1 * | 1/2009 | Bartnik et al. | ............... | 600/301 |

FOREIGN PATENT DOCUMENTS

| | | |
|---|---|---|
| EP | 1 348 375 | 10/2003 |
| GB | 2 089 999 | 6/1982 |
| WO | WO 2004/008959 | 1/2004 |

OTHER PUBLICATIONS

"The Relationship of Alternations in Systolic Time Intervals to Ejection Fraction in Patient's with Cardiac Disease," Garrard, Jr., Circulation, vol. 42 (Sep. 1970) pp. 455-462.
"Measurements of Ejection Fraction by Bioimpedance Method," Capan et al., Brit. Med., vol. 15 (1987), p. 402.

* cited by examiner

*Primary Examiner*—George Manuel
*Assistant Examiner*—Robert N Wieland
(74) *Attorney, Agent, or Firm*—Schiff Hardin LLP

(57) ABSTRACT

In an implantable medical device for detecting and/or monitoring the progression of diastolic heart failure (DHF), and a corresponding method, a parameter is measured that is indicative of left ventricular ejection fraction (LVEF), and a variable is also measured that is indicative of the workload of the patient, and a relation is determined between LVEF and the workload, and DHF is detected and/or the progression of DHF is monitored, dependent on this relation.

31 Claims, 3 Drawing Sheets

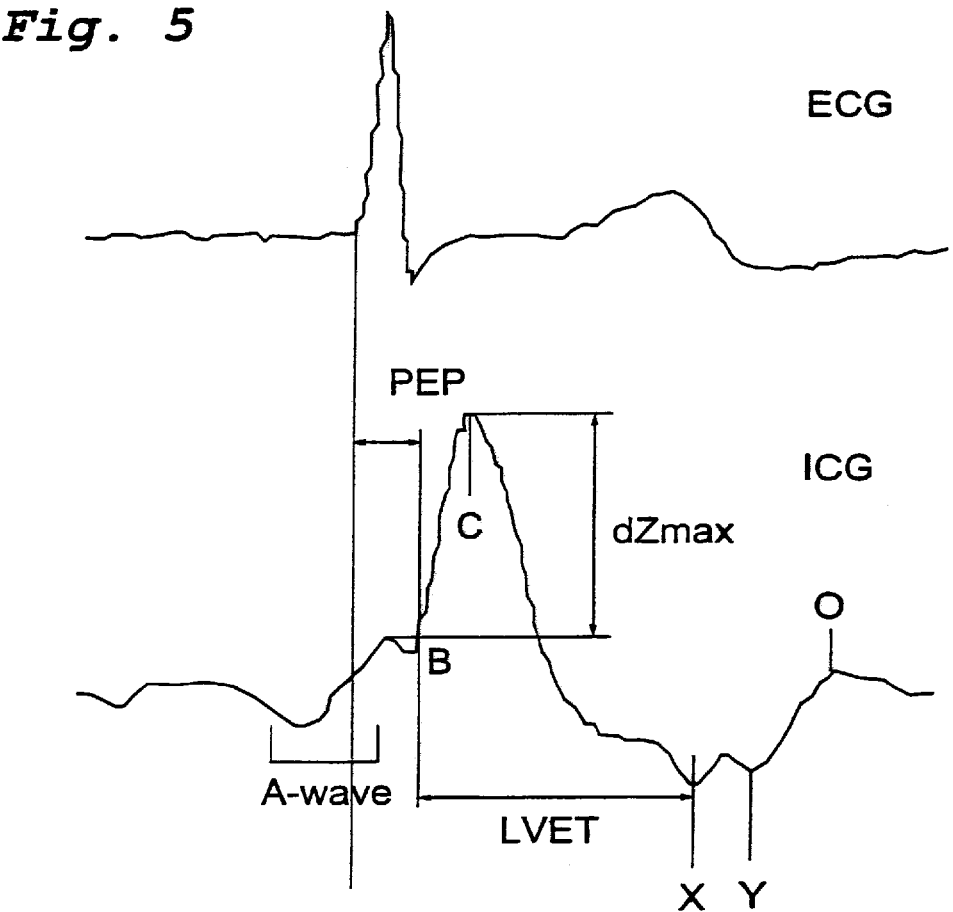

DETECTION AND/OR MONITORING OF DIASTOLIC HEART FAILURE

BACKGROUND OF THE INVENTION

1. Field of the Invention

The present invention relates to an implantable medical device and a method for detecting and/or monitoring the progression of diastolic heart failure, DHF, of a patient. The invention also relates to a heart stimulator provided with such a device.

2. Description of the Prior Art

There is a growing recognition that congestive heart failure caused by a predominant abnormality in the diastolic function, i.e. diastolic heart failure or DHF, is both common and causes significant morbidity and mortality. Therefore, early detection of DHF is important. Patients do not, however, seem to have symptoms at an early stage. In addition, it has been difficult to separate diastolic and systolic heart failure and they may also exist simultaneously.

For diastolic heart failure, DHF, also called heart failure with sustained ejection fraction, EF, no device therapy has appeared to be helpful, as in the case of systolic heart failure, and medication is the only alternative. For the titration of drugs, a measure of the progression or regression of DHF is very valuable.

Approximately 30 to 50 percent of all patients suffering from heart failure have preserved ejection fraction, EF, i.e. are suffering from DHF. DHF is usually defined as a state of disease with the characteristics of heart failure but with an ejection fraction above 50%. The cause of pulmonary edema, liquid retention, weight increase, etc. is diastolic dysfunction, viz. the inability of the heart to relax during diastole.

For healthy persons both EF and the heart rate increase with exercise, thus increasing cardiac output by up to 4.5 times the cardiac output during rest. For heart failure patients, mainly DHF patients, however, the heart rate is increasing with exercise, but EF remains substantially unchanged. The exercise capacity is thus limited for cardiac heart failure (DHF) patients. The greater the change of EF resulting from a change in exercise or workload level of the patient, the less severe the degree of DHF, and vice versa. This is illustrated in FIGS. 1 and 2, which show examples of EF as a function of activity or workload of a healthy subject and a DHF patient respectively. As can be seen from FIG. 1 the workload level of the healthy person has a very strong effect on EF, whereas FIG. 2 shows that the workload level has a little effect on EF, which is typical for DHF patients.

SUMMARY OF THE INVENTION

An object of the present invention is to utilize the above-discussed knowledge a technique for detecting and/or monitoring the progression of DHF by quantifying the effect of exercise or workload on the patient's EF.

The above object is achieved in accordance with the invention by an implantable medical device for detecting and/or monitoring the progression of diastolic heart failure (DHF), and a corresponding method, wherein a parameter is measured that is indicative of left ventricular ejection fraction (LVEF), and a variable is also measured that is indicative of the workload of the patient, and a relation is determined between LVEF and the workload, and DHF is detected and/or the progression of DHF is monitored, dependent on this relation.

Since the workload tolerance and EF variability are patient dependent, the invention is particularly suited for measuring the progression and regression of the DHF. The invention can also preferably be realized by using only already existing hardware of a heart stimulator in the form of (biventricular) pacemaker or ICD. As approximately 30% of systolic heart failure patients also suffer from DHF, a large portion of DHF patients already has a biventricular pacemaker or ICD implanted.

In embodiments of the device according to the invention the measurement unit that measures a variable indicative of the workload of the patient is an accelerometer sensor, or a unit that measures the intrinsic heart rate associated with minute ventilation. Also, combinations of these quantities or all of them can be used to represent the physical workload of the patient.

According to another embodiment of the device according to the invention the unit that measures a parameter indicative of LVEF is an impedance-measuring unit that measures the impedance between electrodes implanted in the patient's heart. As mentioned above a large portion of DHF patients already have a biventricular pacemaker or ICD with its leads implanted, and these leads can then preferably be used for measuring the cardiac impedance.

According to another embodiment of the device according to the invention the unit that measures a parameter indicative of left ventricular ejection fraction, LVEF calculates LVEF from the formula $$\text{LVEF} = k_3 - k_4 \times (\text{PEP/LVET})$$

where $k_3$ and $k_4$ denote predetermined numerical constants, PEP the pre-ejection period, and LVET the left ventricular ejection time. Since an absolute measurement of LVEF is normally not aimed at the absolute values of the constants, $k_3$ and $k_4$ are normally not of primary interest. It would also be possible to use just the quotient between the pre-ejection period, PEP, and LVET as a LVEF surrogate.

In another embodiment of the device according to the invention the unit that measures a parameter indicative of left ventricular ejection fraction, LVEF is a sensor for detecting opening and closing of the aortic valve. An example of such a sensor is a piezoelectric sensor obtained by coating the indifferent ring of an implantable lead with piezoelectric material. With such a sensor both electric and pressure information are obtained from which aortic valve opening and closing can be detected by suitable signal processing.

In other advantageous embodiments of the device according to the invention the unit that determines a relation between LVEF and the workload of the patient are adapted to determine the relation by modeling LVEF as a linear function of the workload, A, i.e.

$$\text{LVEF} = k_1 + k_2 * A$$

where $k_1$ and $k_2$ denote two patient dependent, numerical constants. The unit for determining a relation between LVEF and the workload A of the patient calculate the constant $k_2$ from the formula $$k_2 = \frac{n \sum_{i=1}^{n} A_i E_i - \left( \sum_{i=1}^{n} A_i \right) \left( \sum_{i=1}^{n} E_i \right)}{n \sum_{i=1}^{n} A_i^2 - \left( \sum_{i=1}^{n} A_i \right)^2}$$

where $A_i$ and $E_i$ denote measured workload and ejection fraction values respectively and n the number of measurement values. Thus, LVEF is supposed to be a linear function of the workload, and from a number of measuring points the constants $k_1$ and $k_2$ are determined such that a "best adaption" of the above equation to these measurement points is obtained. By achieving this "best adaption" by minimizing the least square error between measurement points and the formula for LVEF the expression above for $k_2$ is obtained.

In other embodiments of the device according to the invention a memory is provided for storing $k_2$ values. Further, a transmitter is provided for transmitting stored $k_2$ values to an external receiver in connection with follow-up. The transmitter can alternatively transmit stored $k_2$ values to an external receiver automatically on a regular basis. Thus, $k_2$ values are stored in a long-term memory and are transmitted from the device to a programmer at follow-up, or automatically on a regular basis using e.g. a home monitoring system. By transmitting data automatically on e.g. a weekly or daily basis, an important aid in titration of diuretics and other drugs is obtained.

DESCRIPTION OF THE DRAWINGS

FIG. 5 shows a typical ECG and a typical ICG in which timing parameters suitable for use in accordance with the present invention for obtaining a representation of LVEF are defined.

DESCRIPTION OF THE PREFERRED EMBODIMENTS

Figure 1:
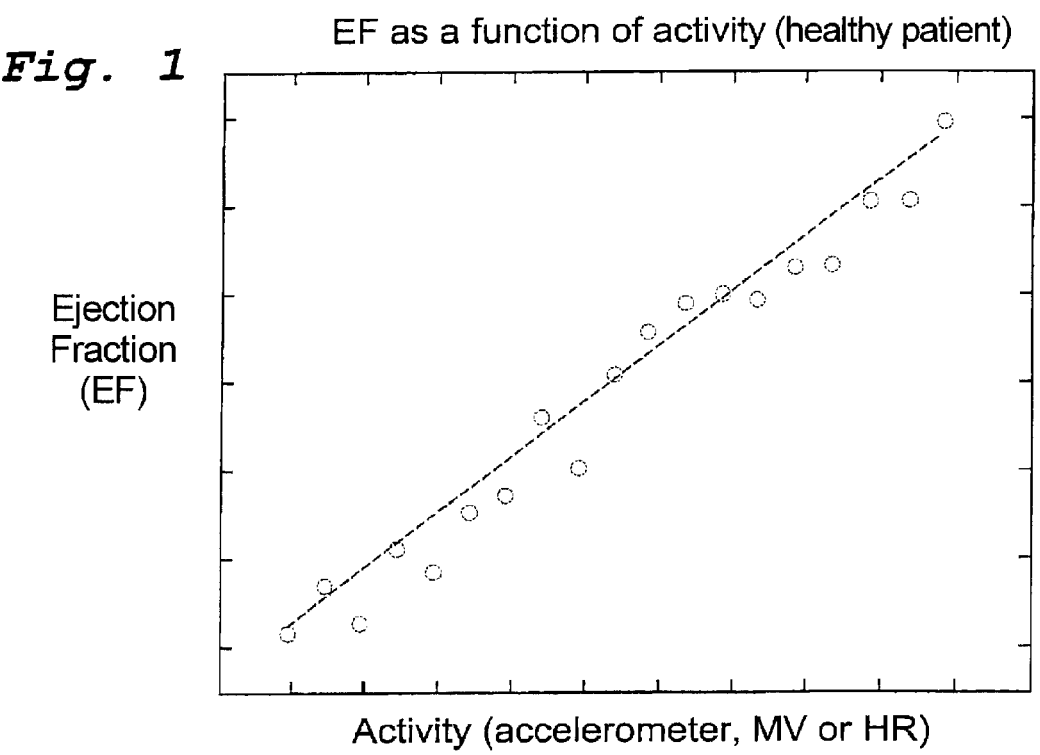
FIG. 1 is a graph showing EF as a function of activity or workload for a healthy subject.
Figure 2:
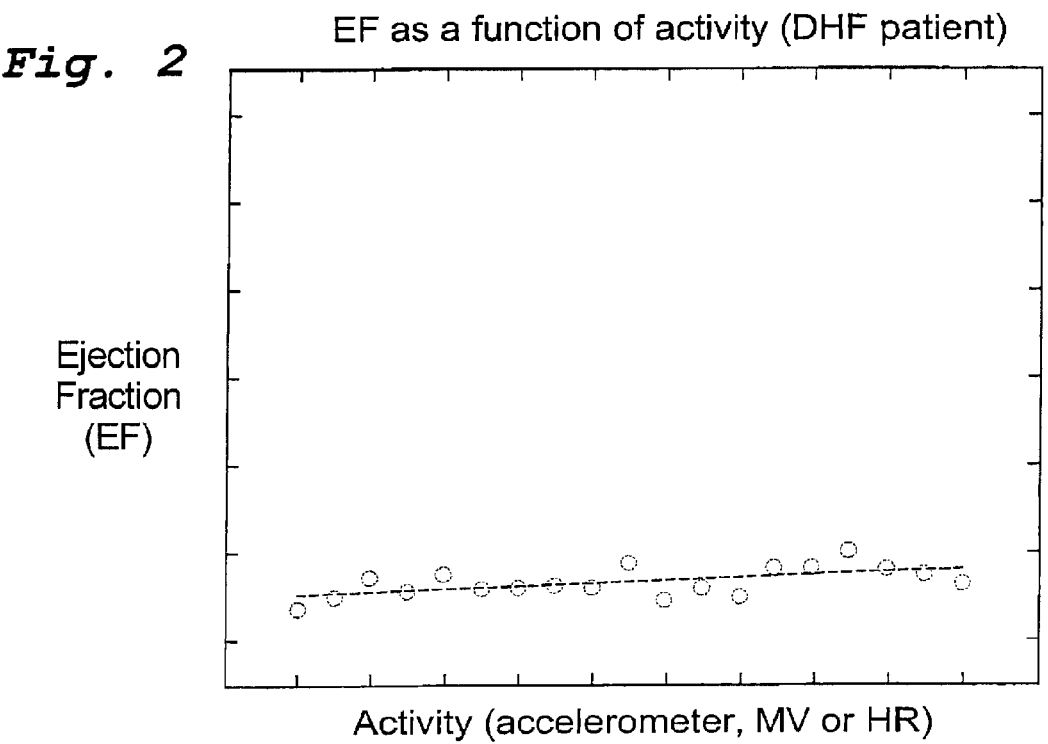
FIG. 2 is a graph showing EF as a function of activity or workload for a patient suffering from DHF.

As mentioned above FIGS. 1 and 2 are diagrams showing EF as a function of activity or workload for a healthy subject and a DHF patient respectively. The workload can be determined with the aid of an accelerometer, by measuring the minute ventilation, MV in the figures, or the intrinsic heart rate, HR. As can be seen from FIG. 1 the workload has a strong effect on EF for a healthy subject, whereas the corresponding effect is very small for a DHF patient, see FIG. 2.

The degree of the workload can be determined from the output of an accelerometer, from the intrinsic heart rate (for patients with a healthy SA node), or from the minute ventilation. Also, combinations of these methods or all of them together can be used for obtaining a surrogate of the workload. The above-mentioned three ways of determining the workload of a person are well known to those skilled in the art and will not be further described in this connection.

Figure 3:
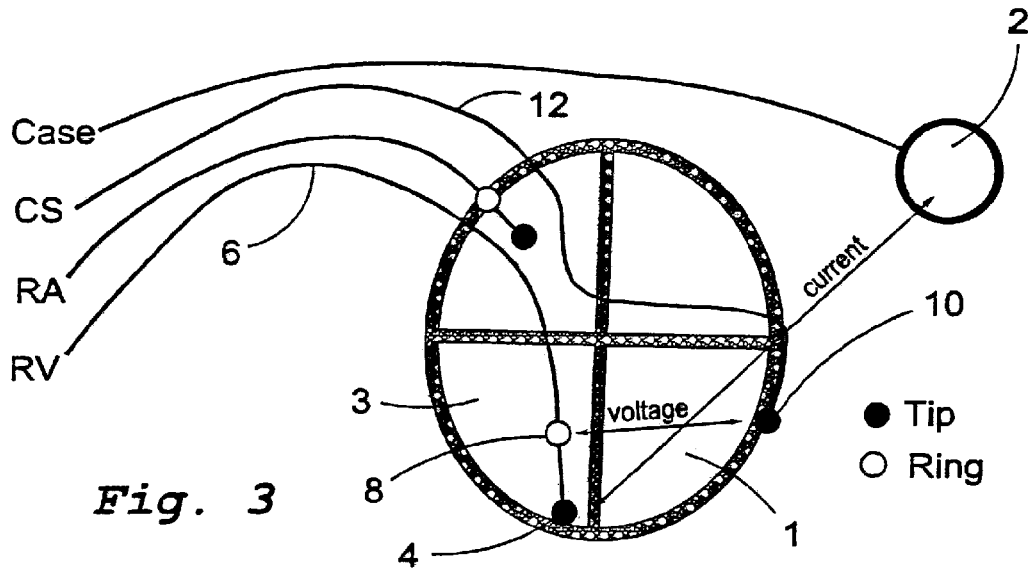
FIG. 3 illustrates a first embodiment of an impedance measurement in accordance with the present invention for determining a representation of the left ventricular volume.
Figure 4:
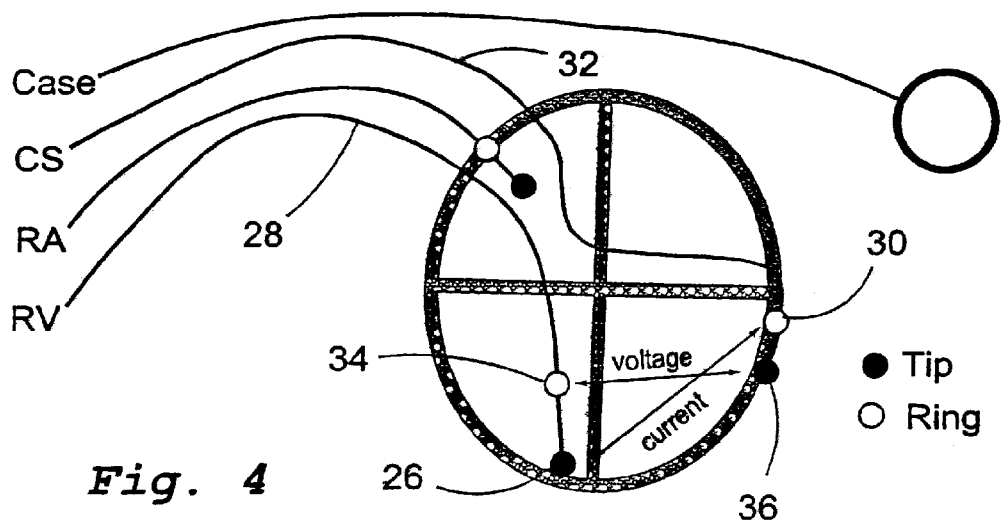
FIG. 4 illustrates a second embodiment of an impedance measurement in accordance with the present invention for determining a representation of the left ventricular volume.

A representation of EF can be obtained by cardiac impedance measurements using implanted leads. For a heart stimulator according to the invention the ordinary leads for sensing and stimulating can preferably be used for this purpose. FIGS. 3 and 4 show two examples of configurations suitable for obtaining a left ventricular volume surrogate.

FIG. 3 thus illustrates an example of impedance measurements between left and right ventricles 1, 3 of a patient's heart. A current is supplied between the pacemaker case, schematically shown at 2, and the tip electrode 4 of a right ventricular lead 6, and the resulting voltage is measured between the ring electrode 8 of the ventricular lead 6 and the tip electrode 10 of a unipolar coronary sinus or felt ventricular lead 12.

FIG. 4 illustrates another embodiment wherein current is supplied between the tip electrode 26 of a bipolar right ventricular lead 28 and the ring electrode 30 of a bipolar coronary sinus lead 32, and the resulting voltage is measured between the ring electrode 34 of the right ventricular lead 28 and the tip electrode 36 of the coronary sinus or left ventricular lead 32.

If no left ventricular lead is present—which would be rare for the heart stimulators for the population of patients in question—a surrogate of EF can be obtained only by using the right ventricular lead.

When the two quantities ejection fraction and workload have been measured, the ejection fraction is modeled as a linear fraction of the workload level, i.e.

$$E = k_1 + k_2 * A$$

where E denotes the measured ejection fraction and $k_1$ and $k_2$ denote two patient dependent, numerical constants. A denotes the measured activity or workload of the patient. The constant $k_2$ which is the constant of interest is determined by minimizing the least square deviation between a number of measurement points and the above linear relation above, $k_2$ will then be given by the formula $$k_2 = \frac{n \sum_{i=1}^{n} A_i E_i - \left(\sum_{i=1}^{n} A_i\right)\left(\sum_{i=1}^{n} E_i\right)}{n \sum_{i=1}^{n} A_i^2 - \left(\sum_{i=1}^{n} A_i\right)^2}$$

where $A_i$ and $E_i$ denote measured workload and ejection fraction values respectively and n the number of measurement values.

Above embodiments are described wherein LVEF is determined by impedance measurements in the patient's heart. Since blood and heart tissue to have different electrical conduction properties, the amplitude of the impedance signal can be used to obtain a surrogate of LVEF. However, there are other possibilities to obtain LVEF surrogates.

According to another embodiment of the invention timing parameters are measured for this purpose. Thus LVEF can be obtained by the formula $$LVEF = k_3 - k_4 \times (PEP/LVET)$$

where $k_3$ and $k_4$ denote predetermined numerical constants, PEP a pre-ejection time period, starting with the onset of a QRS and ending with the opening of the aortic valve, and LVET left ventricular ejection time, starting with the opening and ending with the closing of the aortic valve, see FIG. 5 which shows a typical ECG and the transthoracic impedance, ICG. The transthoracic impedance is not utilized in the invention, but only used for illustrating cardiac events of importance. The cardiogenic impedance is, however, similar to the transthoracic impedance and the same parameters can be extracted from corresponding two impedance curves. The cardiogenic impedance is the impedance measured at higher frequencies, viz. at frequencies of the same order of magnitude as the heart rate (The respiration can be studied in the impedance at low frequencies). The impedance is then usually measured between right tip and ring, such that the impedance in the myocardium itself, and not across the myocardium, is obtained.

The following cardiac events are illustrated in FIG. 5,
A-wave=Contraction of atrium
B=Opening of the aortic valve
C=Maximum systolic flow
X=Closing of the aortic valve
Y=Closing of the pulmonary valve
O=Opening of the mitral valve
PEP=Pre-Ejection Period
LVET=Left Ventricular Ejection Time The numerical values of $k_3$ and $k_4$ in the formula above are according to CL Garrard, Jr., A M Weissler and H T Dodge, "The relationship of alterations in systolic time intervals to ejection fraction in patients with cardiac disease", Circulation, September 1970; 42:455-462, $k_3$=0.84 and $k_4$=0.64, and according to L V Capan et al., "Measurements of ejection fraction by bioimpedance method", Crit Med 1987; 15:402, $k_3$=1.125 and $k_4$=1.25.

Even though the numerical values by Garrard et al. and by Capan et al. differ, the quotient PEP/LVET is used by both. Since it is often not necessary to measure absolute values LVEF the exact values of $k_3$ and $k_4$ are not of importance. It might even possible to use the quotient PEP/LVET as a LVEF surrogate.

The onset of ejection can be detected from the IEGM. The opening and closing of the aortic valve—and thereby PEP and LVET—can be detected in several ways. A so-called Cardium Mechanical Sensor, CMES-sensor, can be used. This is a piezoelectric sensor. The indifferent ring on the lead is coated by piezoelectric material, such that a signal received from this sensor contains both electric and pressure information. The pressure information thus received includes several components. In a certain frequency range the sensor is sensible to, e.g. sound, i.e. it works as a microphone. The signal also contains the true pressure, pressure changes or the time derivative of the pressure. By suitable filtration of the sensor signal valve openings and closings can be detected, since a valve closing is associated with a significant pressure increase and sounds.

Alternatives for detecting aortic valve opening and closing are e.g. by a traditional pressure, by cardiogenic impedance measurements as mentioned above, by sensors picking up heart sounds, i.e. microphones, or by an implantable sensor delivering photo-plethysmographic signals.

Although modifications and changes may be suggested by those skilled in the art, it is the invention of the inventor to embody within the patent warranted heron all changes and modifications as reasonably and properly come within the scope of his contribution to the art.

I claim as my invention:

1. An implantable medical device for detecting and/or monitoring progression of diastolic heart failure DHF of a patient, comprising a first measurement unit that measures in vivo a parameter indicative of left ventricular ejection fraction LVEF, an implantable second measurement unit that measures in vivo a variable indicative of the workload of the patient, an implantable determination unit that determines a relation between LVEF and the workload of the patient, and an implantable DHF unit that detects DHF and/or monitors progression of DHF from said relation.

2. The device according to claim 1, wherein said second measurement unit is an accelerometer sensor.

3. The device according to claim 1 wherein said second measurement unit is a unit that measures the intrinsic heart rate.

4. The device according to claim 1 wherein said second measurement unit is a unit that measures minute ventilation.

5. The device according to claim 1 wherein said first measurement unit is an impedance measuring means for measuring the unit that measures an impedance between electrodes (4,6,8,10,12;26,28,30,32,34,36) implanted in the patient's heart.

6. The device according to claim 5, wherein said impedance measuring unit measures a cardiogenic impedance for detecting opening and closing of the aortic valve.

7. The device according to claim 1 wherein said first measurement unit is a unit that measures a pre-ejection period PEP starting with onset of QRS and ending with opening of the aortic valve, and left ventricular ejection time LVET starting with opening and ending with closing of the aortic valve, and that estimates LVEF from PEP/LVET.

8. The device according to claim 7, wherein said unit that measures a parameter indicative of LVEF calculates LVEF from a formula $$\text{LVEF}=k_3-k_4 \times (\text{PEP/LVET})$$

where $k_3$ and $k_4$ denote predetermined numerical constants.

9. The device according to claim 7 wherein said unit that measures a parameter indicative of LVEF comprises a sensor for detecting opening and closing of the aortic valve.

10. The device according to claim 9, wherein said sensor is a pressure sensor.

11. The device according to 9, wherein said sensor is a sound sensor for picking-up heart sounds.

12. The device according to claim 1 wherein said determination unit determines said relation by modeling LVEF as a linear function of the workload, A, $$\text{LVEF}=k_1+k_2*A$$

where $k_1$ and $k_2$ denote two patient dependent, numerical constants.

13. The device according to claim 12, wherein said DHF unit calculates the constant $K_2$ from the formula $$k_2 = \frac{n\sum_{i=1}^{n} A_i E_i - \left(\sum_{i=1}^{n} A_i\right)\left(\sum_{i=1}^{n} E_i\right)}{n\sum_{i=1}^{n} A_i^2 - \left(\sum_{i=1}^{n} A_i\right)^2}$$

where $A_i$ and $E_i$ denote measured workload and ejection fraction values respectively and n the number of measurement values.

14. The device according to claim 12 comprising a memory is provided for storing $k_2$ values.

15. The device according to claim 14, comprising a transmitter that transmits stored $k_2$ values to an external receiver upon request.

16. The device according to claim 14, comprising a transmitter that transmits stored $k_2$ values to an external receiver automatically on a regular basis.

17. An implantable cardiac stimulator comprising:
an implantable device for detecting and/or monitoring progression of diastolic heart failure DHF of a patient comprising an implantable first measurement unit that measures in vivo a parameter indicative of left ventricular ejection fraction LVEF a second measurement unit that measures a variable indicative of the workload of the patient, an implantable determination unit that determines a relation between LVEF and the workload of the patient, and an implantable DHF unit that detects DHF and/or monitors progression of DHF from said relation and that emits an output corresponding thereto; and an implantable device configured to interact with the patient to deliver cardiac therapy in vivo to the patient dependent on said output.

18. The heart stimulator according to claim 17 comprising a sensor for delivering photo-plethysmographic signals, and wherein said first measurement unit is a unit that measures LVEF from said photo-plethysmographic signals.

19. A device as claimed in claim 17 wherein said first measuring unit is an impedance measuring unit that measures an impedance between electrodes implanted in the patient's heart.

20. A method of detecting and/or monitoring the progression of diastolic heart failure DHF, of a patient, comprising measuring a parameter indicative of left ventricular ejection fraction LVEF, measuring a variable indicative of the workload of the patient, determining a relation between LVEF and workload of the patient, and detecting DHF and/or monitoring progression of DHF from said relation.

21. The method according to claim 20, comprising measuring intrinsic heart rate for determining the workload of the patient.

22. The heart stimulator according to claim 21, comprising a bipolar right ventricular lead and a bipolar left ventricular lead, and wherein said impedance measuring unit comprises a current source for applying a current between a tip electrode of to the right ventricular lead and a ring electrode of the left ventricular lead, and voltage measuring unit for measuring a voltage between ring electrode of the right ventricular lead and a tip electrode of the left ventricular lead resulting from said current.

23. The method according to claim 20, comprising measuring minute ventilation for determining the workload of the patient.

24. The method according to claim 20, comprising measuring a parameter indicative of LVEF by measuring the impedance between electrodes implanted in the patient's heart.

25. The method according to claim 20 by measuring a parameter indicative of LVEF comprises measuring a pre-ejection period PEP, starting from onset of a ORS and ending with the opening of the aortic valve, and left ventricular ejection time starting with opening and ending with closing of the aortic valve, and estimating LVEF from PEP/LVET.

26. The method according to claim 25, comprising calculating LVEF from $$LVEF = k_3 - k_4 \times (PEP/LVET)$$

where $k_3$ and $k_4$ denote predetermined numerical constants.

27. The method according to claim 20 comprising determining said relation between LVEF and workload by modeling LVEF as a linear function of the workload A, $$LVEF = k_1 + k_2 * A$$

where $k_1$ and $k_2$ denote two patient dependent, numerical constants.

28. The method according to claim 27, comprising calculating the constant $k_2$ from $$k_2 = \frac{n \sum_{i=1}^{n} A_i E_i - \left(\sum_{i=1}^{n} A_i\right)\left(\sum_{i=1}^{n} E_i\right)}{n \sum_{i=1}^{n} A_i^2 - \left(\sum_{i=1}^{n} A_i\right)^2}$$

where $A_1$ and $E_1$ denote measured workload and ejection fraction values respectively and n the number of measurement values.

29. The method according to claim 27 comprising storing $k_2$ values and transmitting the stored $k_2$ values to an external receiver upon request.

30. The method according to claim 27 comprising storing $k_2$ values and transmitting the stored $k_2$ values to an external receiver means automatically on a regular basis.

31. The heart stimulator according to claim 19, comprising a stimulating case, a bipolar right ventricular lead and a left ventricular lead and wherein said impedance measuring; unit comprises a current source for applying a current between a tip electrode of the right ventricular lead and the case, and a voltage measuring unit for measuring voltage between a ring electrode of the right ventricular lead and a tip electrode of the left ventricular lead resulting from said current.

* * * * *